| (12) | United States Patent | (10) Patent No.: | US 10,784,343 B2 |
|---|---|---|---|
| | Chen et al. | (45) Date of Patent: | Sep. 22, 2020 |

(54) NANOWIRE FIELD EFFECT TRANSISTOR DETECTION DEVICE AND THE DETECTION METHOD THEREOF

(71) Applicant: ACADEMIA SINICA, Taipei (TW)

(72) Inventors: Chii Dong Chen, Taipei (TW); Li Chu Tsai, Taipei (TW); Chia Jung Chu, Taipei (TW); Ying Pin Wu, Taipei (TW)

(73) Assignee: ACADEMIA SINICA, Taipei (TW)

( * ) Notice: Subject to any disclaimer, the term of this patent is extended or adjusted under 35 U.S.C. 154(b) by 356 days.

(21) Appl. No.: 15/856,325

(22) Filed: Dec. 28, 2017

(65) Prior Publication Data

US 2019/0206990 A1 Jul. 4, 2019

(51) Int. Cl.

| H01L 29/06 | (2006.01) |
|---|---|
| C12Q 1/6825 | (2018.01) |
| C12Q 1/6874 | (2018.01) |
| G01N 27/414 | (2006.01) |
| B82Y 40/00 | (2011.01) |
| H01L 29/78 | (2006.01) |
| G01N 27/48 | (2006.01) |

(52) U.S. Cl.
CPC ......... *H01L 29/0669* (2013.01); *B82Y 40/00* (2013.01); *C12Q 1/6825* (2013.01); *C12Q 1/6874* (2013.01); *G01N 27/4145* (2013.01); *G01N 27/4146* (2013.01); *G01N 27/48* (2013.01); *H01L 29/78* (2013.01)

(58) Field of Classification Search
None
See application file for complete search history.

(56) References Cited

U.S. PATENT DOCUMENTS

2017/0336347 A1 11/2017 Ram et al.

OTHER PUBLICATIONS

Li et al.; "Effect of Nanowire Number, Diameter, and Doping Density on Nano-FET Biosensor Sensitivity", Aug. 4, 2011, Fabrication of Nano-FET Arrays (Year: 2011); ACS Nano.*
Gao et al.; "Multiplexed Dectection of lung cancer biomarkers in patients serum with CMOS-compatible silicon nanowire arrays"; vol. 91 Biosensors and Bioelectronics, May 15, 2017, 3.1 SiNW device fabrication and 3.2 Detection principle (Year: 2016); Science direct.*

(Continued)

*Primary Examiner* — Jeffry H Aftergut
*Assistant Examiner* — Jaeyun Lee
(74) *Attorney, Agent, or Firm* — Bacon & Thomas, PLLC (57) ABSTRACT

The present invention discloses a Nanowire Field Effect Transistor Detection Device and the Detection Method thereof. The Nanowire Field Effect Transistor Detection Device of the present invention comprises: gate oxide, SiNW chip, surface oxide, and surface molecule layer. The circuit structure of the Nanowire Field Effect Transistor Detection Device comprises a first resistor, a second resistor, a first capacitor, a second capacitor, a third capacitor, a fourth capacitor, an AC voltage source, and an ammeter. In addition, the present invention provides a method for attaching the probe Ni-NTA to the Nanowire Field Effect Transistor Detection Device. Furthermore, the present invention provides a method for attaching the isooctyl trimethoxysilane molecule to the Nanowire Field Effect Transistor Detection Device.

1 Claim, 13 Drawing Sheets

(56) References Cited

OTHER PUBLICATIONS

"Highly sensitive and selective label-free detection of cardiac biomarkers in blood serum with silicon nanowire biosensors"; Zhang et al, Dec. 7-9, 2009, A. Surface functrionalization (Year: 2009); IEEE.*

Ying-Pin Wu et al., "Detection of electrically neutral and nonpolar molecules in ionic solutions using silicon nanowires", Mar. 22, 2017, Nanotechnology 28 (2017) 165501 (8pp).

* cited by examiner

| | $\Delta A \Uparrow$ | $\Delta A \Downarrow$ |
|---|---|---|
| $\Delta \theta \Uparrow$ | I ($\Delta F \Uparrow$, $\Delta \varepsilon \pm$) | $\text{II}_\alpha$ ($\Delta F \uparrow$, $\Delta \varepsilon ++$)<br>$\text{II}_\beta$ ($\cancel{\Delta F}$, $\Delta \varepsilon +$)<br>$\text{II}_\gamma$ ($\Delta F \downarrow$, $\Delta \varepsilon ++$) |
| $\Delta \theta \Downarrow$ | $\text{III}_\alpha$ ($\Delta F \uparrow$, $\Delta \varepsilon --$)<br>$\text{III}_\beta$ ($\cancel{\Delta F}$, $\Delta \varepsilon -$)<br>$\text{III}_\gamma$ ($\Delta F \downarrow$, $\Delta \varepsilon --$) | IV ($\Delta F \Downarrow$, $\Delta \varepsilon \pm$) |

NANOWIRE FIELD EFFECT TRANSISTOR DETECTION DEVICE AND THE DETECTION METHOD THEREOF

BACKGROUND

1. Field of the Invention

The present invention relates to a detection device and the detection method, particularly to a nanowire field effect transistor detection device and the detection method thereof.

2. Description of the Prior Art

In the Nanowire Field Effect Transistor (NWFET) sensors field, the charge field produced by the surface molecules change upon the probe/target interaction, thus changing the conductance of the nanowire.

However, in most detection applications, including biosensors and chemical sensors, the molecular species are in an ionic solution. Normally, when the molecular charge configuration is quite complex, the molecular charge field will decay exponentially, with the characteristic length described by Debye screening potential. Furthermore, there are target molecules that possess no net dipole moment, and these molecules will fall into a category named nonpolar.

Examples of nonpolar organic molecules comprises hexane, toluene, tetrachloromethane and many others. In addition, there are neutral molecules, such as ethylene glycol, that carry no net charge. Moreover, there are zwitterion molecules having net charge varies with the pH value of the solution.

At a specific pH value, called the isoelectric point (pI), zwitterions carry no net charge and are electrically neutral. These molecules may interact with probe molecules through van der Waals and hydrophobic interactions. Although the detection of volatile organic compounds in a gaseous environment using a specific probe molecule has been reported, the underlying mechanism is not concluded. Furthermore, the detection of such interactions in a solution environment is left unexplored. In the present invention, the abovementioned "interactions" are not used as the detection method.

Normally, a physical quantity is well known as molecular permittivity, which is a measure of how a molecule opposes an external electric field. It is noted that the permittivity varies with the conformation and composition of the molecules, and hence it always changes if molecular interaction takes place. The proposed technique is to detect this permittivity change using the alternating current measurement technique (the AC technique).

Unlike the conventional AC impedance method, in which alternating current flows through the electrolyte between two measurement electrodes, the alternating current only flows in the nanowire sensors between the source and drain electrodes. According to the changes in the complex impedance, the physical properties of the interaction can be analyzed, and allowing the characterization and classification of interactions.

As in the conventional case, when a nonpolar molecule in a phosphate buffer solution (PBS) with pH=pI is used as an example of a neutral molecule, the technique can be applied to the Nanowires with and without a surface oxide. On the one hand, it is compatible with nanowire sensors in which the wires are not electrically isolated from the solution, such as in the cases of ZnO nanowires and carbon nanotubes. On the other hand, provided that the nanowire is semiconducting and is covered with an insulating layer, the proposed AC technique preserves the inherent sensing capability of the NWFETs.

Thus, the abovementioned "Nanowire Field Effect Transistor Detection Device" uses the field effect mechanism to detect the charge (or molecular field) change produced by the reaction of surface molecules with very high detection sensitivity. If the reacting molecules using the van der Waals force or hydrophobic interaction force, such as the electrically neutral or nonpolar molecules, there will be no charge (or molecular field) change and it will be unable to use the field effect transistor to conduct the detection. Generally speaking, the existence of these molecules will endanger the human health and safety, as the harmful molecules. Thus, how to grasp suitable detection technique to detect these harmful molecules effectively will be quite urgent and unsolved problem at present.

Inasmuch as the foregoing considered, in order to satisfy the long-term demand of the industry, it is necessary to develop a new and effective detection device and method to provide the demand of detection market. Meanwhile, it is also necessary to research and develop the Nanowire Field Effect Transistor Detection Device and the detection method thereof, in order to increase the detection speed, reduce the detection time, and increase the detection accuracy.

SUMMARY

The Nanowire Field Effect Transistor Detection Device of the present invention comprises: gate oxide, SiNW chip, surface oxide, and surface molecule layer (because the "SiNW chip" defined in the present invention can comprise the "surface oxide layer" or exclude the "surface oxide layer", so that it is very suitable to use the "SiNW chip" in the present invention).

The circuit structure of Nanowire Field Effect Transistor Detection Device comprises a first resistor, a second resistor, a first capacitor, a second capacitor, a third capacitor, a fourth capacitor, an AC voltage source, and an ammeter. Wherein, the first resistor and the first capacitor are connected in series type to form a first circuit, then the second capacitor and the third capacitor are connected to form a second circuit, and the second resistor, the AC voltage source, and the ammeter are connected to form a third circuit.

The present invention provides a method for attaching the probe Ni-NTA to the Nanowire Field Effect Transistor Detection Device. The SiNW chip is first immersed in 2% nitric acid solution, and then immersed in a 2% APTES solution. The chip is then rinsed with deionized (DI) water and bake-dried. The chip is reacted with 12.5% glutaraldehyde in 0.1×PBS, and then rinsed thoroughly with DI water. This is then followed by immersion in 2% AB-NTA free acid. Subsequently, ethanolamine is added to react with the unreacted glutaraldehyde. Finally, a polydimethylsiloxane slab is bonded to the chip, and a 1% nickel sulfate solution is introduced into the fluidic channel to react with the surface molecules. This is then purged with a 0.1×PBS buffer into the fluidic channel.

In addition, the present invention provides a method for attaching the isooctyl trimethoxysilane molecules to the Nanowire Field Effect Transistor Detection Device. Firstly, the SiNW chip is first immersed in 2% nitric acid solution and then 2% IOTMS solution. The chip is then rinsed with DI water and blow-dried with nitrogen ($N_2$). Finally, the chip is bake-dried to promote the attachment of IOTMS on the surface of the SiNWs.

The present invention uses the time-varying electric field technique to detect the vector impedance change, and provides the real-time information of molecules reaction.

The present invention not only can conduct the detection in a gaseous environment, but also can detect the "neutral" and "nonpolar" molecules in a liquid environment.

The "Nanowire Field Effect Transistor Detection Device" of the present invention uses the field effect mechanism to detect the charge (or molecular field) change produced by the reaction of surface molecules.

The present invention presents a technique for the detection of neutral, charged, polar and nonpolar molecules in a gaseous (or liquid) environment.

The present invention can be applied to highly sensitive "disease in vitro detection", "biological molecules (DNA, amino acid, protein) detection", "drug residue detection", "food additive detection", "genetically modified food detection", "hazardous chemicals detection", "environmental pollutants" and "microorganism detection" etc.

The present invention can use the wire or membrane of various conductors or semiconductors, including "carbon nanotube", "zinc oxide" or "gallium nitride" etc.

The present invention can be used in any covered (or uncovered) and insulated semiconductor wire or membrane.

Therefore, the advantage and spirit of the present invention can be understood further by the following detail description of invention and attached figures.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

The attached figures should be used to describe the implement method of the present invention. In the figures, the same element symbol is used to represent the same element. In order to describe the element more clearly, its size or thickness might be scaled.

Attachment of the Probe Ni-NTA to the Nanowire Field Effect Transistor Detection Device in the Present Invention:

As for the attachment of the probe Ni-NTA to the Nanowire Field Effect Transistor Detection Device in the present invention, first providing a SiNW chip, then the SiNW chip is immersed in 2% nitric acid solution for about 5 minutes.

Then, the SiNW chip is immersed in a 2% APTES ((3-aminopropyl) triethoxysilane, Sigma-Aldrich, purity 99%) solution for about 1 hour.

And then, the SiNW chip is rinsed with deionized (DI) water and bake-dried at 110° C. for about 1 hour.

The SiNW chip is reacted with 12.5% glutaraldehyde (Sigma-Aldrich, 25%) in 0.1×PBS (13.7 mM NaCl, 0.27 mM KCl, 1 mM $Na_2HPO_4$, 0.2 mM $KH_2PO_4$) for about 1 hour, and then rinsed thoroughly with deionized (DI) water.

The SiNW chip is followed by immersion in 2% AB-NTA free acid (N-(5-amino-1-carboxypentyl) iminodiacetic acid) for about 1 hour.

Subsequently, ethanolamine is added to react with the unreacted glutaraldehyde so as to block the unwanted reaction.

Continuously, a Polydimethylsiloxane (PDMS) slab is bonded to the SiNW chip, and a 1% nickel sulfate solution is introduced into the fluidic channel to react with the surface molecules for 30 minutes.

In the final step, a 0.1×PBS buffer is used into the fluidic channel.

In the present invention, after attachment of the isooctyl trimethoxysilane molecules to the SiNW chip, the SiNW chip can possess the function of chemical adsorption or physical adsorption with the specific biochemical molecules, and the invention can conduct real-time detection of specific biochemical molecules.

As for the attachment of the isooctyl trimethoxysilane (IOTMS) to the Nanowire Field Effect Transistor Detection Device in the present invention, first providing a SiNW chip, then the SiNW chip is first immersed in 2% nitric acid solution for about 5 minutes.

Then the SiNW chip is immersed in a 2% IOTMS solution for about 1 hour to form a monolayer of isooctyl trimethoxysilane molecule on the surface.

The SiNW chip is then rinsed with deionized (DI) water and blow-dried with nitrogen ($N_2$) to remove the unbounded molecules.

Finally, the SiNW chip is bake-dried at 110° C. for about 1 hour to promote the attachment of isooctyl trimethoxysilane on the surface of the SiNWs.

Figure 1:
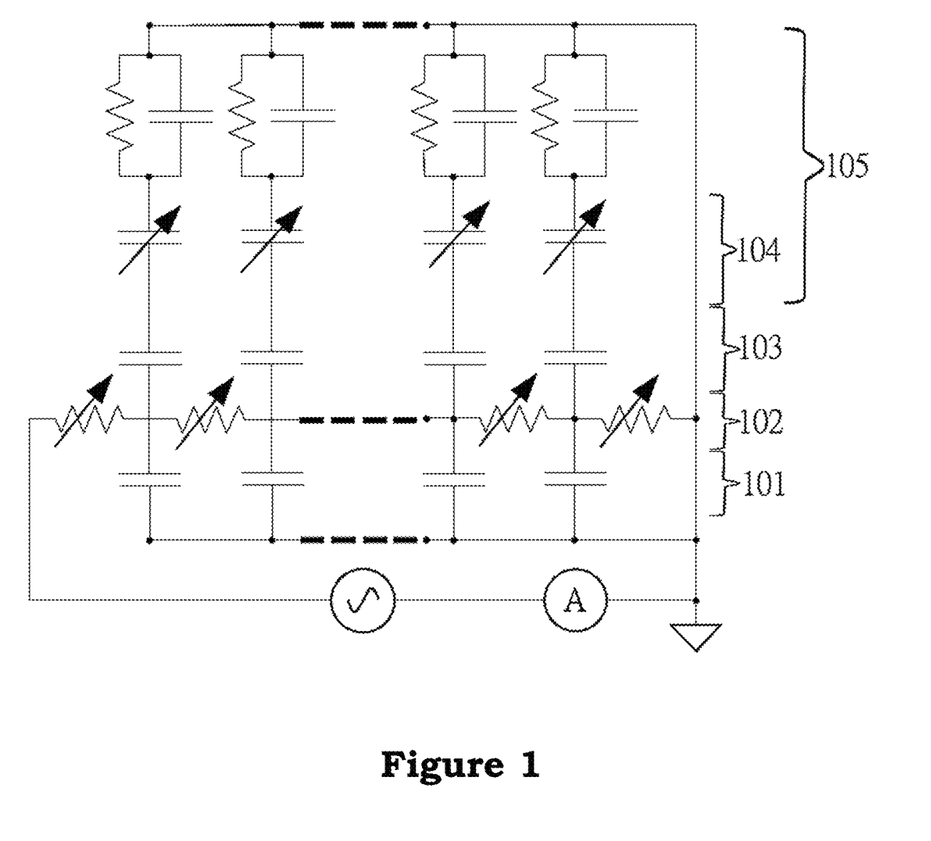
FIG. 1 illustrates the cross-sectional view of the fabricated Nanowire Field Effect Transistor Detection Device provided by the present invention.

The (Electronic) Circuit Structure of the Nanowire Field Effect Transistor Detection Device in the Present Invention:

FIG. 1 illustrates the cross-sectional view of the fabricated Nanowire Field Effect Transistor Detection Device provided by the present invention, comprising gate oxide 101, SiNW chip 102, surface oxide 103, and surface molecule layer 104. FIG. 1 also schematically shows contact of p-type silicon nanowire and aqueous solution 105.

As shown in FIG. 1, the SiNW chip 102 is located on the gate oxide 101, the surface oxide 103 is located on the SiNW chip 102, and the surface molecule layer 104 is located on the surface oxide 103.

As shown in FIG. 1, the Nanowire Field Effect Transistor Detection Device of the present invention is fabricated on commercially available silicon-on-insulator (SOI) wafers using electron-beam lithography. The nanowire is covered by the insulting oxide layer and capacitively coupled to the back-gate electrode through underneath gate oxide. The nanowire uses the sinusoidal oscillating source-drain voltage to generate the bias for measuring the current of nanowire.

As shown in FIG. 1, in the structure of Nanowire Field Effect Transistor Detection Device of the present invention, the nanowire is about 3 μm long, 115 nm wide and 200 nm thick, and the source/drain electrodes are doped the extra boron in order to reduce electrode resistance. The concentration of nanowire remains the same as that of the original carrier concentration of about ~$9 \times 10^{14}$ cm$^3$. This concentration corresponds to a sheet resistivity of 15 Ω-cm, and the resistance of nanowires is about 20 MΩ.

As shown in FIG. 1, in the structure of Nanowire Field Effect Transistor Detection Device of the present invention, the electrical contact (not shown in the figure) between Au bonding pads and the underneath source/drain layers may be of Schottky type, which is responsible for the observed low conductance values. The backside of the SiNW chips is coated with a metal layer that serves as the backgate electrode. Micro-fluidic channels made of Polydimethylsiloxane (PDMS) are bonded to the nanowire chip to guide aqueous solution to the SiNWs.

Still as shown in FIG. 1, in the structure of Nanowire Field Effect Transistor Detection Chip of the present invention, the components in the circuit are explained as follows: the nanowire is modeled as a variable resistor shunted by the underneath gate capacitor. The resistance varies when the interaction induces a change in the molecular field. Above the nanowire, a thin surface oxide represents the top gate capacitance. Beyond this, the surface-attached probe molecule layer behaves as a dielectric and is modeled as a molecular capacitor in series between the top gate capacitance and the ionic aqueous solution. After interaction, the permittivity of the probe/target hybrid molecules changes, and hence the molecular capacitance is represented by a variable capacitor. This change in the effective capacitance leads to the variations in both amplitude and phase. On the top of the molecule layer, there is an ionic aqueous solution that acts as a conductive dielectric, and is thus modeled as a resistively shunted capacitor.

As shown in FIG. 1, in the structure of Nanowire Field Effect Transistor Detection Chip of the present invention, the complex nanowire impedance can be represented by two real variables, namely, amplitude and phase. The measurement electronics can also be operated in DC mode, enabling a comparison between the AC and DC signals.

Figure 2:
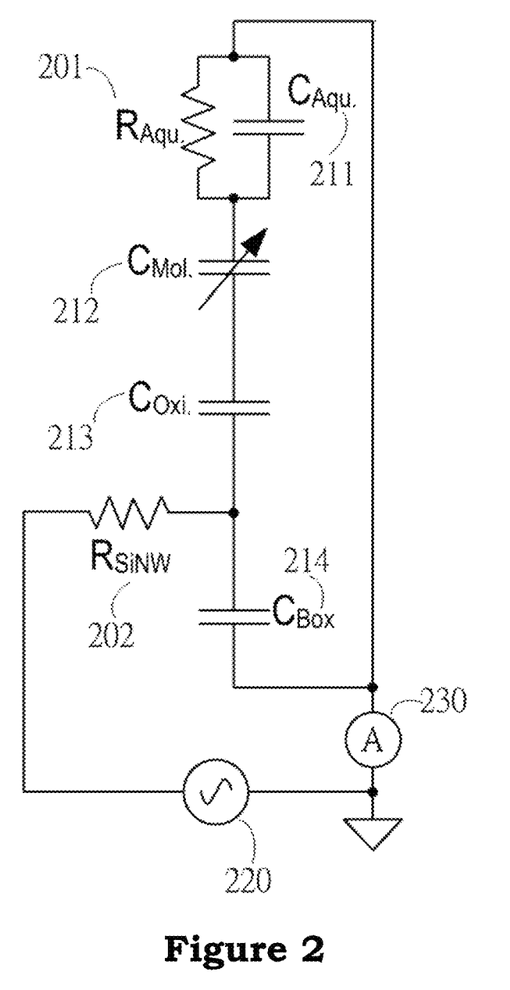
FIG. 2 illustrates the AC circuit of the fabricated Nanowire Field Effect Transistor Detection Device provided by the present invention.

FIG. 2 illustrates the AC circuit of the fabricated Nanowire Field Effect Transistor Detection Device provided by the present invention. It is a circuit in series, including nanowire, oxide, surface molecule layer and aqueous solution. The structure of Nanowire Field Effect Transistor Detection Device in the present invention includes a first resistor ($R_{Aqu.}$) 201, a second resistor ($R_{SiNW}$) 202, a first capacitor ($C_{Aqu.}$) 211, a second capacitor (or called variable resistor) ($C_{Mol.}$) 212, a third capacitor ($C_{Oxi.}$) 213, a fourth capacitor ($C_{BOX}$) 214, an AC voltage source 220, and an ammeter 230.

As shown in FIG. 2, in the structure of Nanowire Field Effect Transistor Detection Chip of the present invention, the first resistor ($R_{Aqu.}$) 201 and the first capacitor ($C_{Aqu.}$) 211 are connected in series to form a first circuit, then the second capacitor (or called variable resistor) ($C_{Mol.}$) 212 and the third capacitor ($C_{Oxi.}$) 213 are connected to form a second circuit, and the second resistor ($R_{SiNW}$) 202, the AC voltage source 220, and the ammeter 230 are connected to form a third circuit.

It is known that the suffix of "Aqu" represents aqueous, "Mol" represents molecule, "Box" represents buried oxide beneath SiNW, "Oxi" represents SiNW surface oxide layer. The detection method for Nanowire Field Effect Transistor Detection Device of the present invention:

FIG. 2 illustrates the AC circuit of the fabricated Nanowire Field Effect Transistor Detection Device provided by the present invention. Its detection method includes the following steps:

As shown in the following Equation 1, according to the model circuit of FIG. 2, the complex impedance can be obtained by Equation 1 from AC voltage source 220. Because the AC circuit includes the capacitor C, its impedance comprises the real part R and the imagery part X, and j=√−1, thus, after calculating impedance with the serial, and the shunt, the complex impedance can be obtained from AC voltage source 220.

$$Z_{unit} = R_{unit} - jX_{unit} = \quad \text{Equation 1}$$

$$\left[ \left( \frac{R_{Aqu.}(-jX_{C_{Aqu.}})}{R_{Aqu.} + (-jX_{C_{Aqu.}})} \right) + (-jX_{C_{Mol.}}) + (-jX_{C_{Oxi.}}) \right] \cdot$$

$$\frac{(-jX_{C_{Box}})}{\left[ \left( \frac{R_{Aqu.}(-jX_{C_{Aqu.}})}{R_{Aqu.} + (-jX_{C_{Aqu.}})} \right) + (-jX_{C_{Mol.}}) + (-jX_{C_{Oxi.}}) \right] + (-jX_{C_{Box}})} +$$

$$\frac{R_{SiNW} \cdot (-jX_{C_{SiNW}})}{R_{SiNW} + (-jX_{C_{SiNW}})}$$

The phase angle of unit is obtained from the following Equation 2. According to the model circuit of FIG. 2, the complex impedance can be obtained by Equation 2 from AC voltage source 220 to get the phase angle (θ). It is defined as tan (θ)=(−X/R), where R and X are the real part and the imagery part of the complex impedance.

$$\theta_{unit} = \tan^{-1} \frac{-X_{unit}}{R_{unit}} \quad \text{Equation 2}$$

For a uniform nanowire, the impedance of the entire circuit can be obtained from the following Equation 3. The impedance of AC circuit in FIG. 1 will be equal to the complex impedance from AC voltage source 220 in FIG. 2. The main reason is that the circuit in FIG. 1 is the model circuits in FIG. 2 are connected in series.

$$\frac{1}{Z_{circuit}} = \sum \frac{1}{Z_{unit(i)}} = \frac{n}{Z_{unit(i)}} \qquad \text{Equation 3}$$

Since the number of units, n, is a real number, the phase angle of the entire circuit is the same as that of each unit, $\theta_{circuit}=\theta_{unit}$. Although all resistors and capacitors in the model circuit contribute to the phase angle θ, there are two major contributors to the phase angle θ. These two components are the capacitive reactance $X_{CMol}$ and wire resistance $R_{SiNW}$; they arise respectively from changes in the dielectric and the charges of the surface molecule layer. For a quantitative analysis, numeric calculation is performed based on Equation 1.

Figure 3A:
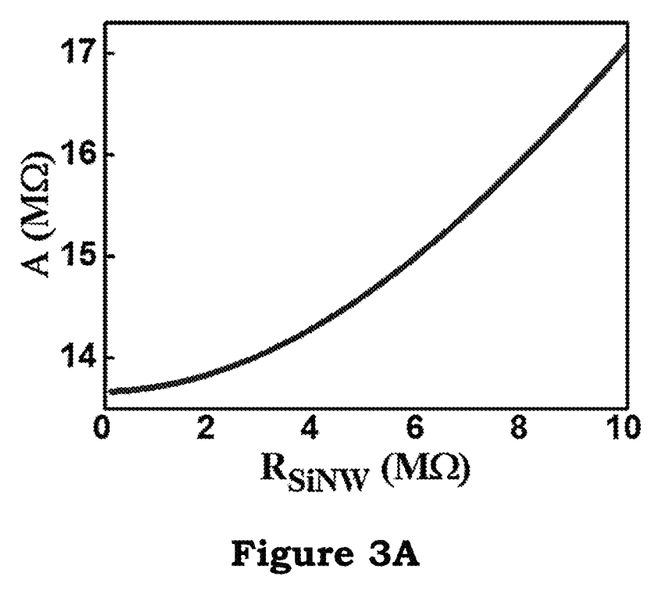
FIG. 3A and FIG. 3B illustrate the curve diagrams of the present invention.
Figure 3B:
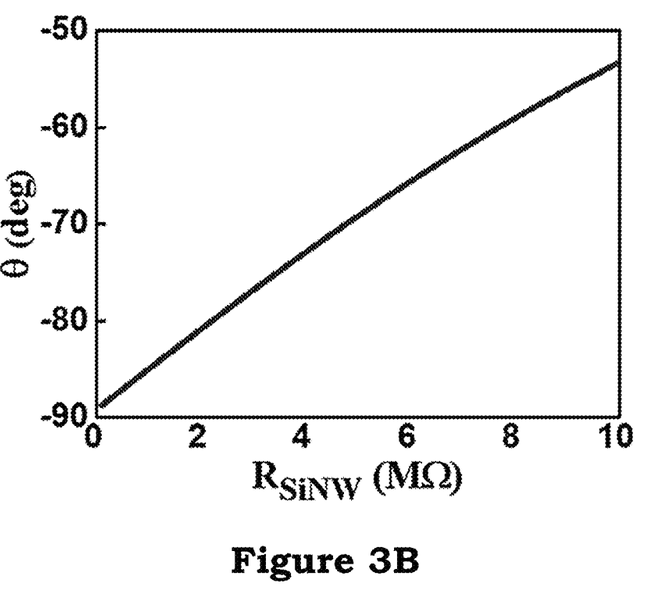

From the calculation of abovementioned Equation 1, Equation 2, and Equation 3, the curves (diagrams) of FIG. 3A and FIG. 3B can be obtained. When the resistance of SiNW is increased, the measured amplitude A of AC will be higher, and the phase angel change Δθ will be approaching zero.

Figure 4A:
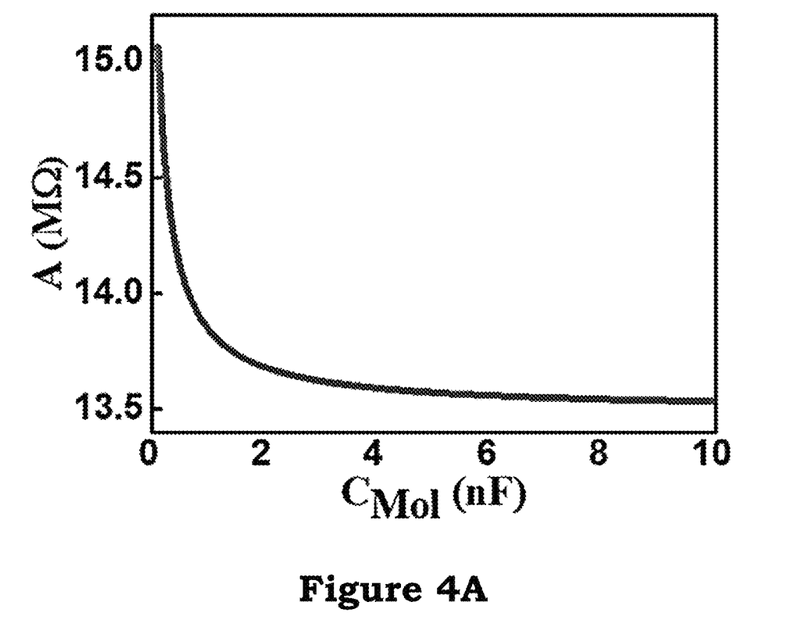
FIG. 4A and FIG. 4B illustrate the curve diagrams of the present invention.
Figure 4B:
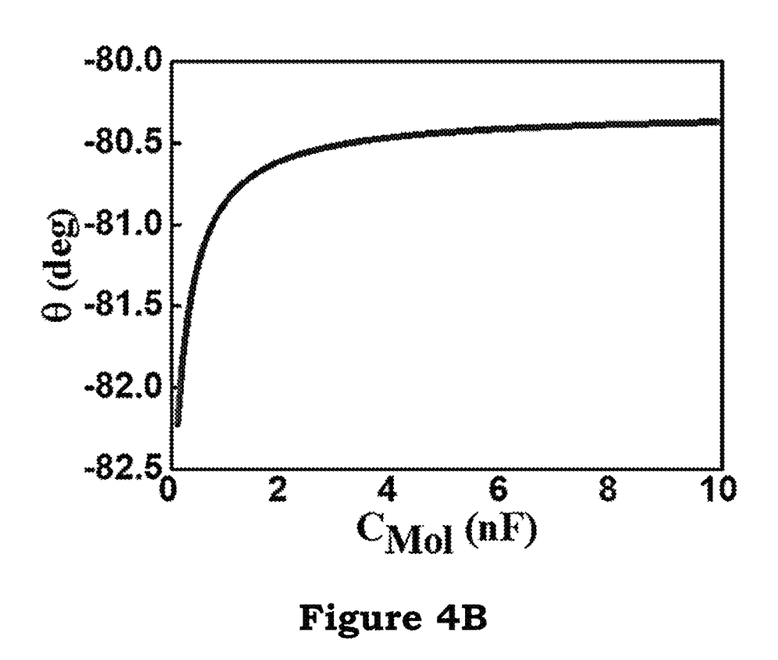

In addition, from the curves (diagrams) of FIG. 4A and FIG. 4B, it is found that when the effective capacitance of molecular layer is increased, the measured amplitude A of AC will be lower, and the phase angel change Δθ will be approaching zero, but does not change much.

Figure 5:
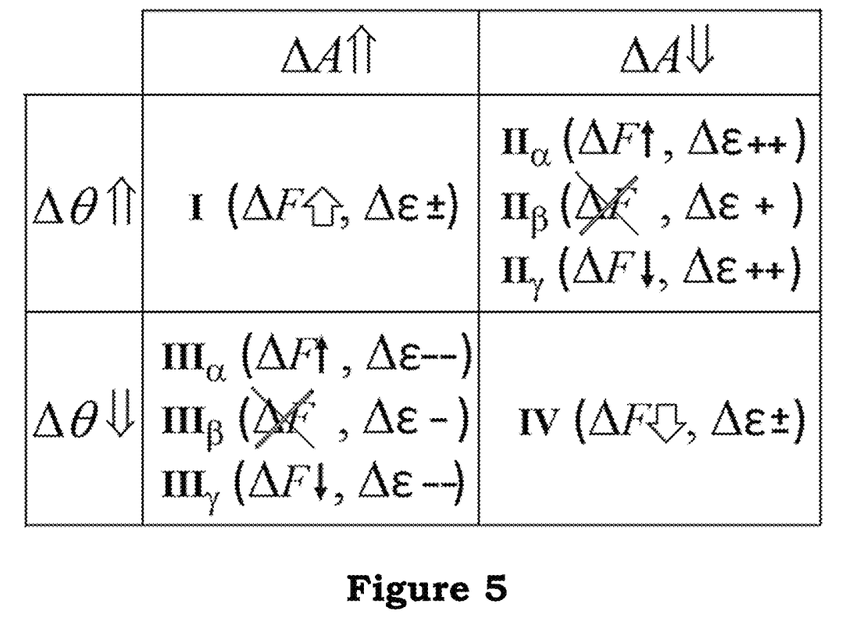
FIG. 5 illustrates the property comparison diagram of the present invention.

From the calculation of abovementioned Equation 1, Equation 2, and Equation 3, the property comparison diagram of FIG. 5 can be obtained. From FIG. 5, it is found that the change of molecular charge ΔF and the change of molecular permittivity Δε generated from molecules reaction can be judged and compared by the change of measured ΔA and Δθ. So whether the nature of molecules reaction is Coulomb force or van der Waals force can be found.

The present invention uses the time-varying electric field technique to detect the vector impedance change, and provides the real-time information of molecules reaction. It is to detect the chemical reaction between the probe molecules and the target molecules, so as to detect the vector impedance change. The principle is that this chemical reaction will cause the change of molecular permittivity and represents in the vector impedance change. So the present invention also can provide the real-time information of molecules reaction.

In the conventional AC impedance method, the alternating current flows through the electrolyte between two measurement electrodes. Unlike the conventional AC impedance method, the alternating current (AC) of the present invention only flows through the nanowire sensors between the source electrode and the drain electrode.

The method provided by the present invention can be used to expand the detection function of Field Effect Transistor Detection sensors for detecting the neutral molecules or nonpolar molecule, such as nonpolar hexane and electrically neutral histidine. From the measured vector impedance and phase, it is able to judge the essence of molecular reaction, including the change of molecular field and molecular permittivity.

In the present invention, histidine is an amino acid that is commonly used as a tag for binding with nickel-nitrilotriacetic acid (Ni-NTA), the latter of which is a linking molecule for the protein purification process. Ni-NTA is immobilized on the surface of the nanowire to act as a histidine capture molecule. It is noted that the hydrogen binding configurations, and thus the net molecular charges, are different for the histidine in Poly(butylene succinate) (PBS) with pH values greater than, equal to and smaller than the pI value.

Figure 6A:
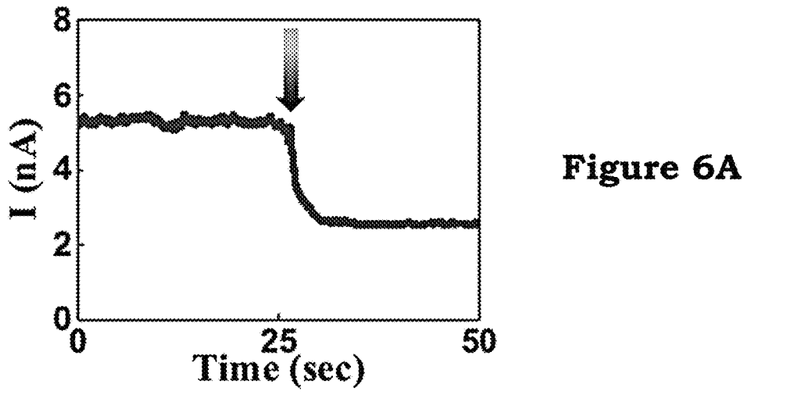
FIG. 6A, FIG. 6B and FIG. 6C illustrate the real-time detection results of histidine in an embodiment of the present invention.
Figure 6B:
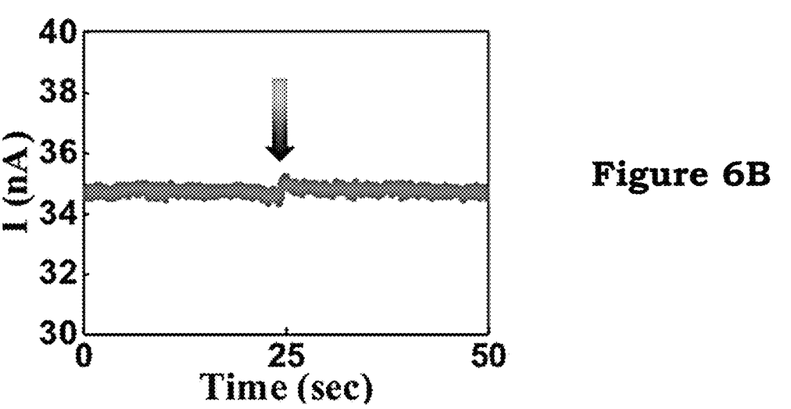
Figure 6C:
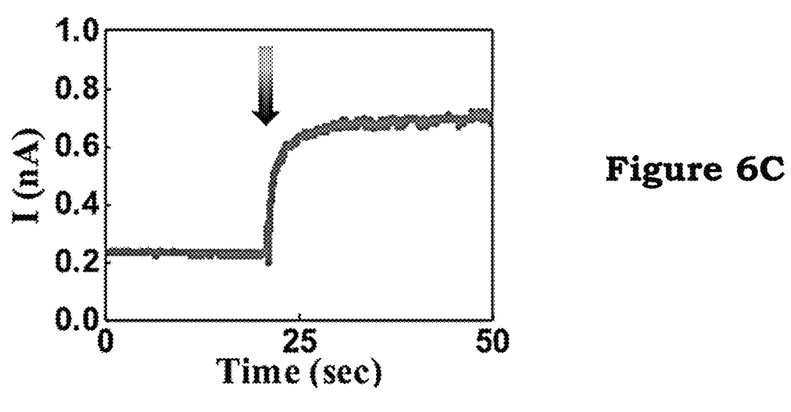

FIG. 6A, FIG. 6B, and FIG. 6C show the real-time detection of histidine using the DC technique at three different pH values. When pH<pI, histidine has a net positive charge, and hence a decrease in the current of a p-type nanowire FET sensor. In contrast, when pH>pI the current should increase. Indeed, the DC current responded as expected. Furthermore, when pH=pI, the DC current did not show any change because of the neutrality of the histidine. The same experiments are performed using the AC technique, in which the nanowires are biased by an AC source, and the nanowire AC current is measured and is described by both amplitude and phase quantities.

Figure 7A:
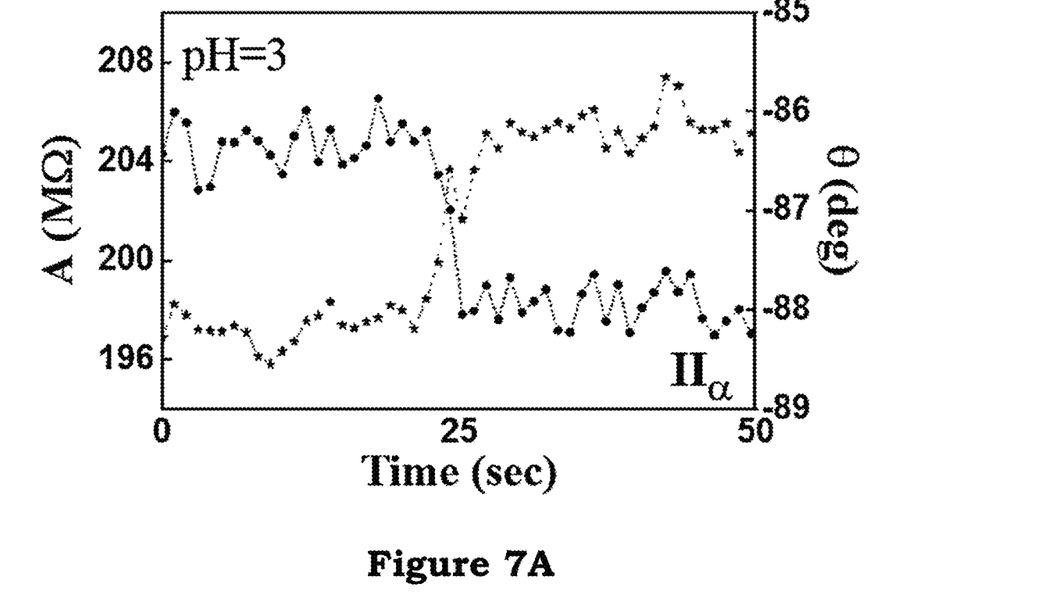
FIG. 7A, FIG. 7B and FIG. 7C illustrate a clear increase in the relative phase of current to the phase of the applied bias voltage in an embodiment of the present invention.
Figure 7B:
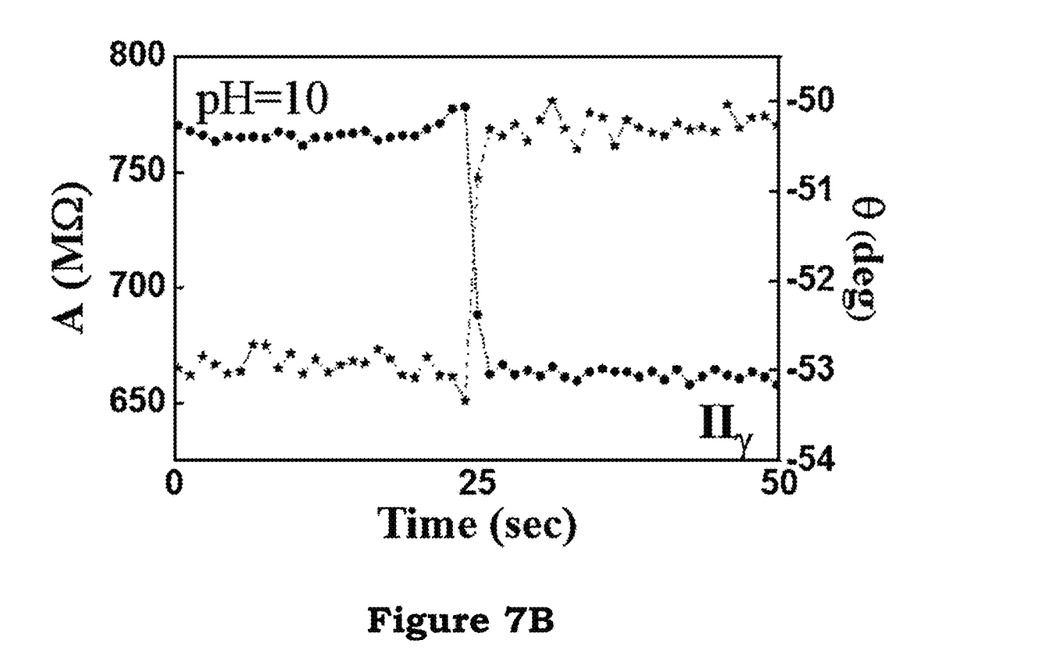
Figure 7C:
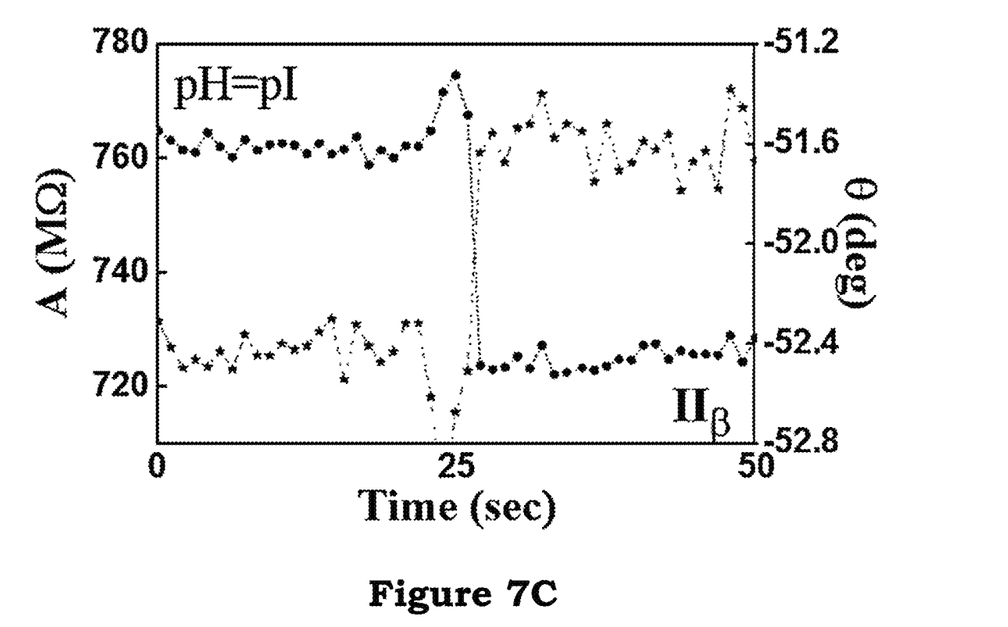

As shown in FIG. 7A, FIG. 7B, and FIG. 7C, a clear increase in the relative phase of current to the phase of the applied bias voltage is observed regardless of the pH values. The fact that the phase changes, even for the case of pH=pI, is evidence of the change in the molecular permittivity. Based on this analysis, the permittivity of histidine bound with a Ni-NTA molecule is higher than that of Ni-NTA alone. To show that this permittivity change is not caused by non-specific interaction to histidine, a control experiment is performed, in which nickel sulfate is not added to the AB-NTA free acid, so that there is no Ni-ion available for binding.

Figure 7D:
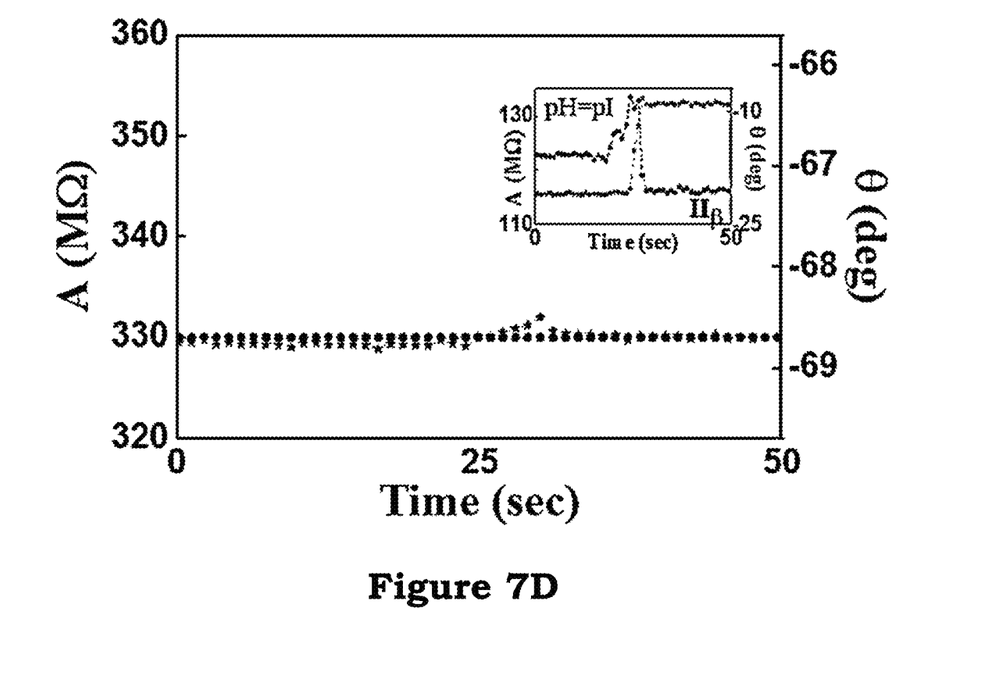
FIG. 7D illustrates an achieved detection concentration for histidine of 1 pM in an embodiment of the present invention.

As shown in FIG. 7D, FIG. 7D shows an achieved detection concentration for histidine of 1 pM, and no change in the amplitude or phase is observed.

Figure 8A:
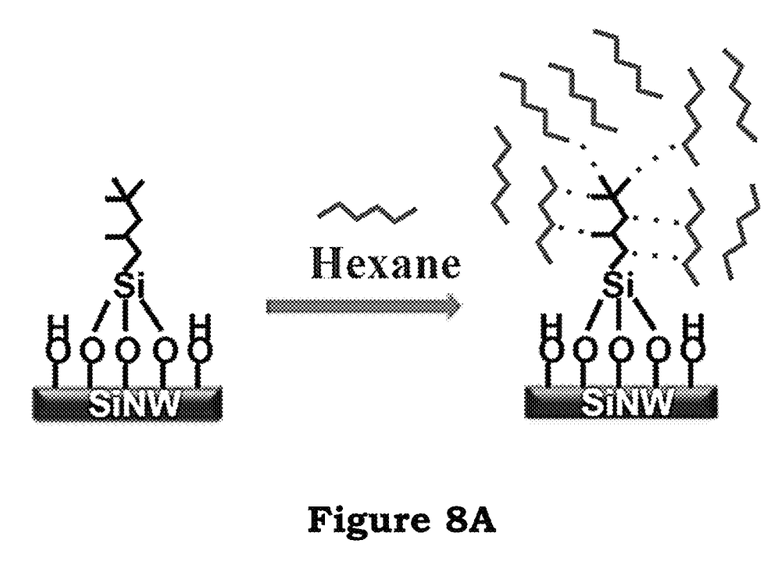
FIG. 8A illustrates schematically the hydrophobic interaction between isooctyl trimethoxysilane and hexane in an embodiment of the present invention.

FIG. 8A illustrates schematically the hydrophobic interaction between isooctyl trimethoxysilane (IOTMS) and hexane. In the present invention, hexane is used to demonstrate the detection of nonpolar molecules. Hexane is an aliphatic molecule in the alkane family, and is liquid at room temperature. It is injected into the IOTMS (isooctyltrimethoxysilane)-modified nanowires through a PDMS fluidic channel.

Figure 8B:
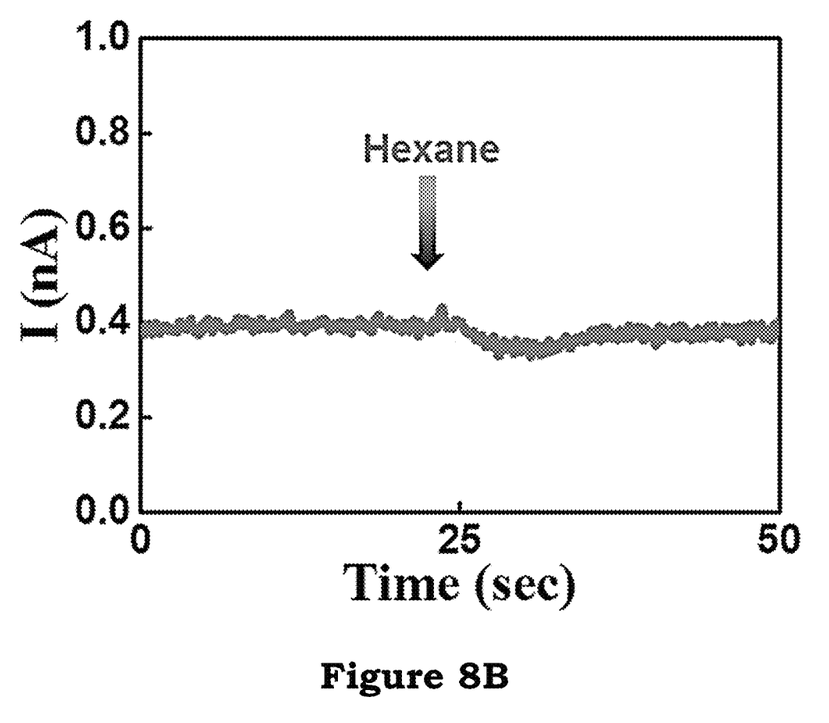
FIG. 8B and FIG. 8C illustrate the nanowire response to DC and AC biases in an embodiment of the present invention.
Figure 8C:
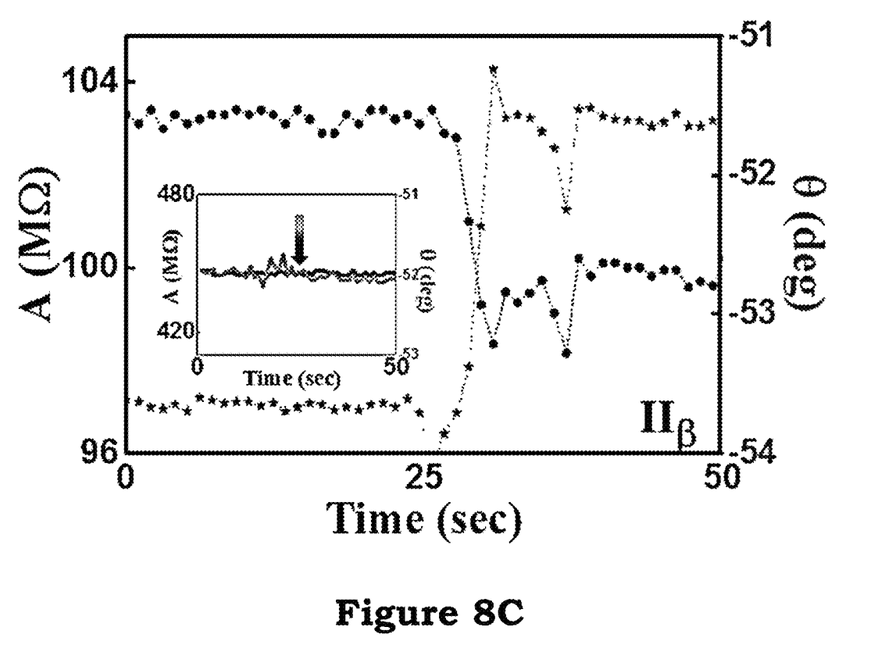

FIG. 8B and FIG. 8C show the nanowire response to DC and AC biases. The nanowire did not show any apparent change in DC current on the injection of hexane due to the lack of molecular field. However, when using the AC technique, a clear jump in the phase of the nanowire current is observed, signifying a change in the permittivity of the surface molecules.

As shown in FIG. 8C, in a control experiment utilizing the AC technique, the same experiment is performed using unmodified bare nanowires, and the wire exhibited no change in either amplitude or phase. The force of interaction between hexane and isooctyl trimethoxysilane (IOTMS) is the van der Waals force, which possesses no selectivity amongst the molecules.

Figure 8D:
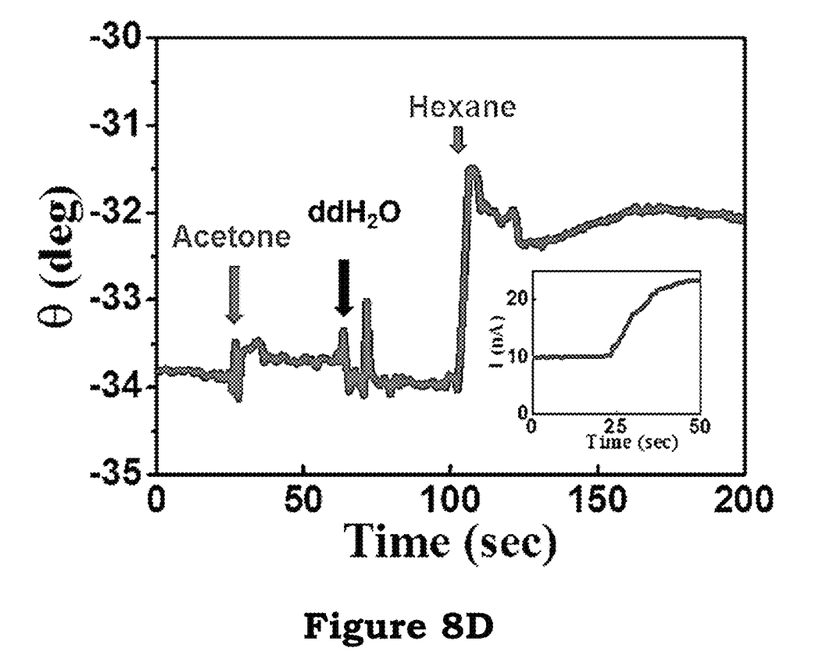
FIG. 8D illustrates schematically the interaction between isooctyl trimethoxysilane and acetone in an embodiment of the present invention.

In FIG. 8D it is observed that the interaction between isooctyl trimethoxysilane (IOTMS) and acetone can also induce a phase change, even though this change is much smaller than that of hexane. Furthermore, the isooctyl trimethoxysilane (IOTMS)-acetone interaction can also be detected using the DC technique, as displayed in the inset in FIG. 8D, due to the weak but nonzero polarity of acetone.

Figure 9A:
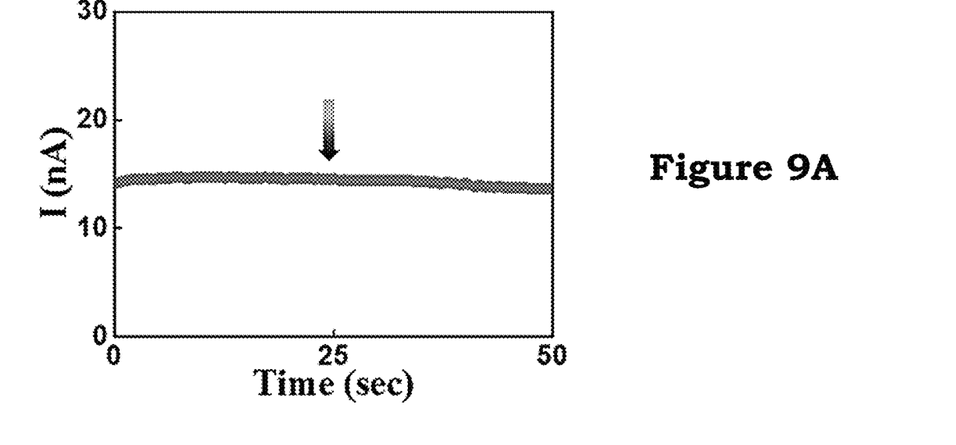
FIG. 9A, FIG. 9B and FIG. 9C illustrate that the AC technique has the capability to detect various weak nonpolar molecules in an embodiment of the present invention.
Figure 9B:
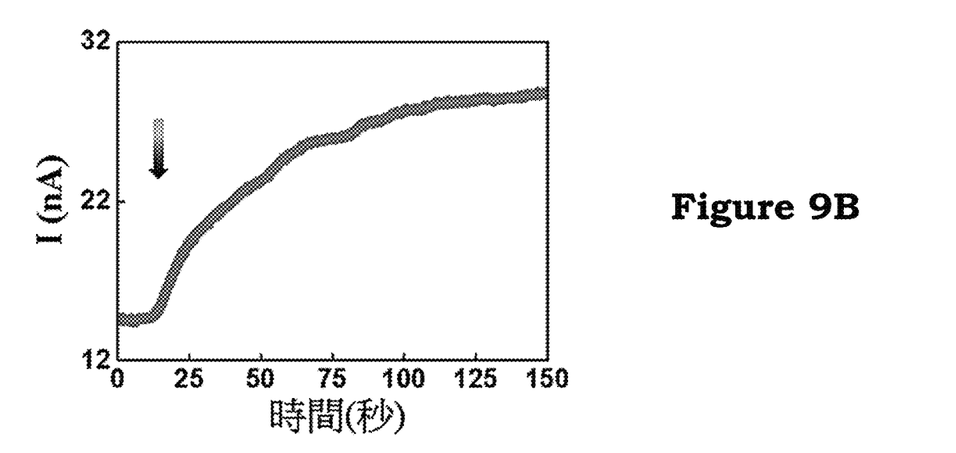
Figure 9C:
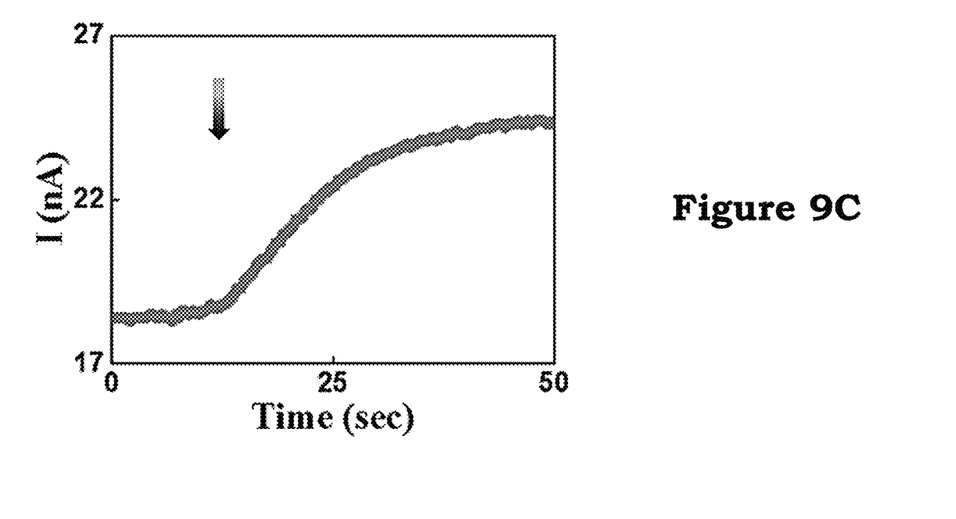

As shown in FIG. 9A, FIG. 9B, and FIG. 9C, to demonstrate the capability of the AC technique in the detection of various weak polar molecules, the detection of ethylene, ethylene glycol, methanol and isopropyl alcohol are performed using isooctyl trimethoxysilane (IOTMS) as the probe molecule. In the case of the DC measurement, both methanol and isopropyl alcohol displayed increased current, whereas the ethylene glycol displayed an undetectable current.

Figure 9D:
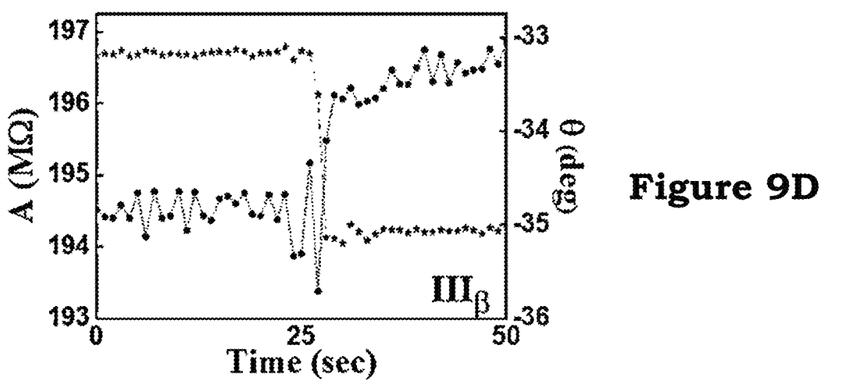
FIG. 9D, FIG. 9E and FIG. 9F illustrate that in the AC measurement the amplitude change and the phase change showed the opposite signs in an embodiment of the present invention.
Figure 9E:
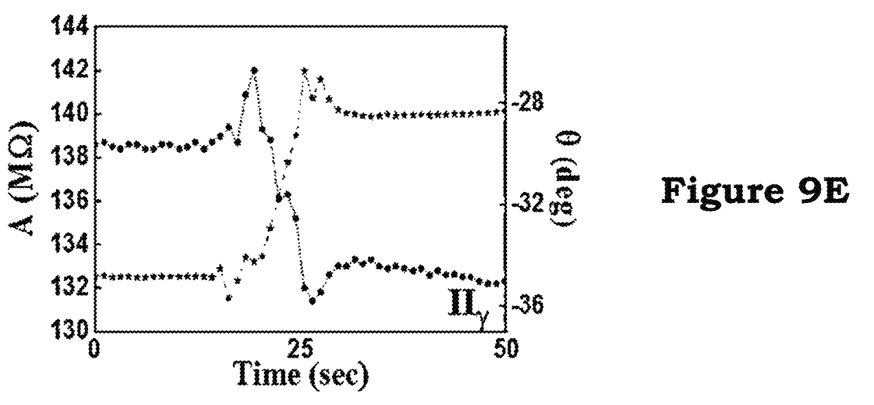
Figure 9F:
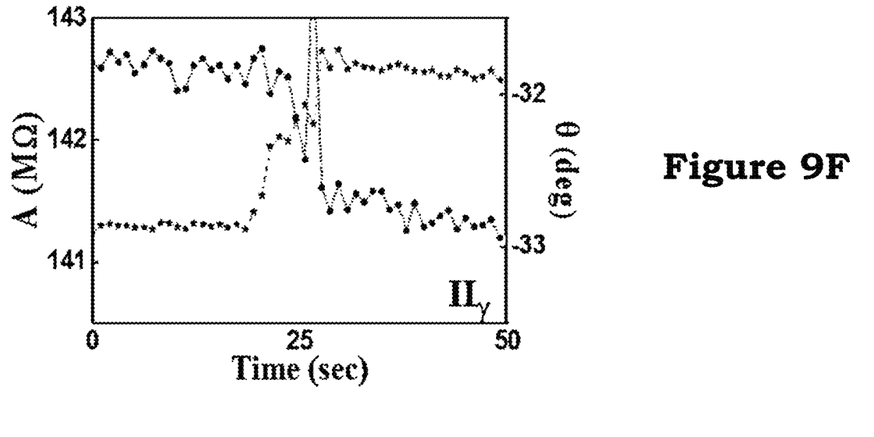

As shown in FIG. 9D, FIG. 9E, and FIG. 9F, in the AC measurement, both impedance change and phase angle change showed the opposite sign. It is found that impedance change increased on the introduction of ethylene glycol, but decreased for the cases of methanol and isopropyl alcohol.

Figure 10A:
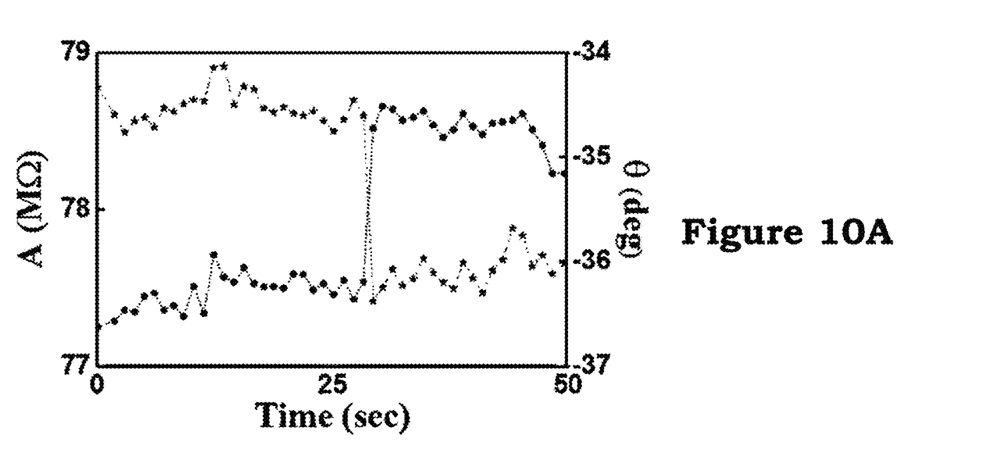
FIG. 10A and FIG. 10B illustrate the clear variations in the amplitude and phase in an embodiment of the present invention.
Figure 10B:
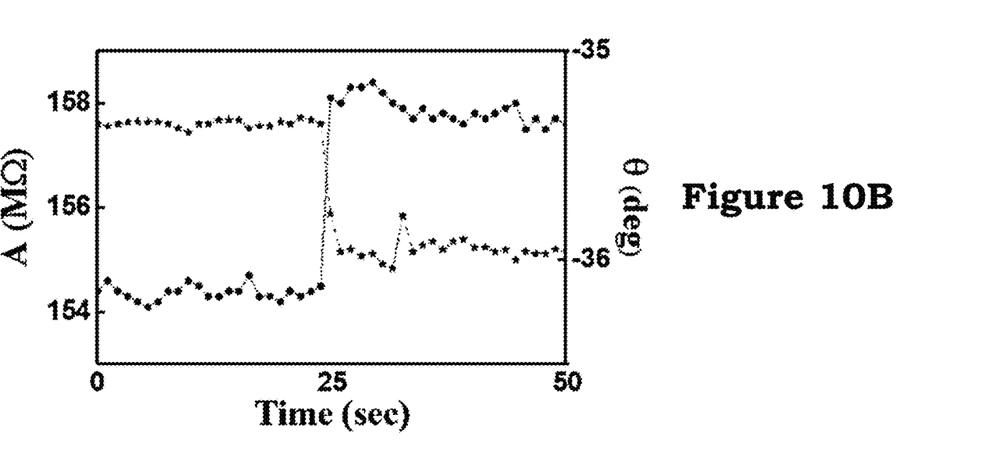

As shown in FIG. 10A and FIG. 10B, clear variations in the amplitude and phase are observed in both experiments. A control experiment is performed to confirm that the measured amplitude and phase changes are due to the change in the nanowire complex impedance rather than the solution.

Figure 10C:
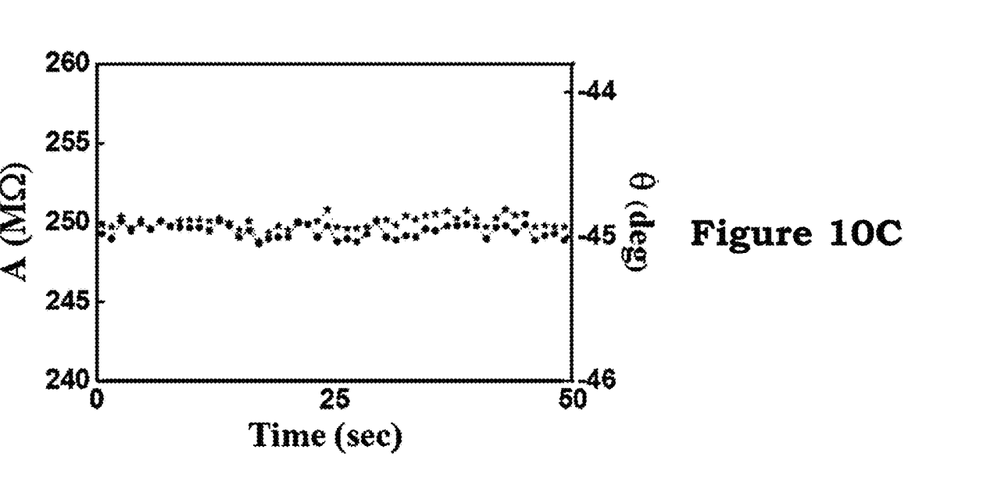
FIG. 10C illustrates nickel sulfate is not added to AB-NTA free acid to ensure the absence of the $Ni^{2+}$ binding site in an embodiment of the present invention.

In the control experiment shown in FIG. 10C, nickel sulfate is not added to AB-NTA free acid to ensure the absence of the $Ni^{2+}$ binding site, and the nanowire showed no change in the complex impedance. With this, the AC technique is applicable for non-FET-based sensors.

The insulating layer covering the surface of SiNW is essential for the operation of conventional Field Effect Transistor (FET) sensors in an aqueous environment, because it prevents the charge transfer between the solution/molecule ions and the silicon conduction channel. However, the nanowires (and carbon nanotubes) with no surface-insulating layer can still function as a sensor, even though the origin of the resistance change is quite different. This change may be for two possible reasons: namely, the change in the nanowire surface charge states and the charge transfer between nanowires and surface molecules. Below that, this resistance change, as well as any change in the molecular permittivity, can be detected using the AC technique. To do this, the $SiO_2$ layer on the wire surface is intentionally removed by using a buffered oxide etch solution. The wire is thereafter employed for the detection of histidine and hexane.

The present invention presents an AC technique for the detection of neutral, charged, polar and nonpolar molecules, while keeping the advantages of nanowire sensors which are label free, and have high sensitivity and real-time detection. This technique is complementary to the conventional DC technique and extends the possibility to the detection of various molecules. The detection of nonpolar hexane molecules as well as weak polar molecules such as acetone, ethylene glycol, methanol and isopropyl alcohol are demonstrated. The achieved sensitivity for the detection of electrically neutral histidine is 1 pM. Together with the information gained from both the DC and AC measurements, the nature of molecular interactions, including the changes in molecular field and in permittivity, which serves as a basis for the classification of interactions. Lastly, this AC technique is applicable for sensors with bare semiconductor nanowires and carbon nanotubes, in which the surface insulating layer is absent.

The Nanowire Field Effect Transistor Detection Device of the present invention uses the field effect mechanism to detect the charge (or molecular field) change produced by the reaction of surface molecules. The present invention not only can conduct the detection in a gaseous environment, but also can detect the "neutral" and "nonpolar" molecules in a liquid environment. The present invention presents a technique for the detection of neutral, charged, polar and nonpolar molecules in a gaseous (or liquid) environment.

The present invention can be used in any covered (or uncovered) and insulated semiconductor wire or membrane. The present invention can use the wire or membrane of various conductors or semiconductors, including "carbon nanotube", "zinc oxide" or "gallium nitride" etc. Furthermore, the present invention can be applied to highly sensitive "disease in vitro detection", "biological molecules (DNA, amino acid, protein) detection", "drug residue detection", "food additive detection", "genetically modified food detection", "hazardous chemicals detection", "environmental pollutants" and "microorganism detection" etc.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A method for attaching a probe Ni-NTA (Nickel-Nitrilotriacetic Acid) to a Nanowire Field Effect Transistor Detection Device, comprising:
    providing a SiNW (Silicon Nanowire) chip;
    immersing said SiNW (Silicon Nanowire) chip in 2% nitric acid solution for about 5 minutes;
    immersing said SiNW (Silicon Nanowire) chip in a 2% APTES ((3-aminopropyl) triethoxysilane, Sigma-Aldrich, purity 99%) solution for about 1 hour;
    rinsing said SiNW (Silicon Nanowire) chip with a deionized (DI) water and bake-dried said SiNW (Silicon Nanowire) chip at 110° C. for about 1 hour;
    reacting said SiNW (Silicon Nanowire) chip with 12.5% glutaraldehyde (Sigma-Aldrich, 25%) in 0.1×PBS (phosphate buffer solution) (13.7 mM NaCl, 0.27 mM KCl, 1 mM $Na_2HPO_4$, 0.2 mM $KH_2PO_4$) for about 1 hour, rinsing thoroughly with said deionized (DI) water;
    immersing said SiNW (Silicon Nanowire) chip in 2% AB-NTA free acid (N-(5-amino-1-carboxypentyl) iminodiacetic acid) for about 1 hour;
    adding ethanolamine;
    bonding a Polydimethylsiloxane (PDMS) slab to said SiNW (Silicon Nanowire) chip, and a 1% nickel sulfate solution being introduced into a fluidic channel to react with a surface molecules for 30 minutes; and
    purging with a 0.1×PBS (phosphate buffer solution) buffer into said fluidic channel.

* * * * *